(12) United States Patent
Kang

(10) Patent No.: US 12,318,305 B2
(45) Date of Patent: Jun. 3, 2025

(54) HEIGHT-ADJUSTABLE INTERVERTEBRAL FUSION CAGE

(71) Applicant: L&K BIOMED CO., LTD., Yongin-si (KR)

(72) Inventor: Gook Jin Kang, Seoul (KR)

(73) Assignee: L&K BIOMED CO., LTD., Yongin-si (KR)

( * ) Notice: Subject to any disclaimer, the term of this patent is extended or adjusted under 35 U.S.C. 154(b) by 332 days.

(21) Appl. No.: 17/777,164

(22) PCT Filed: Sep. 25, 2020

(86) PCT No.: PCT/KR2020/013088
§ 371 (c)(1),
(2) Date: May 16, 2022

(87) PCT Pub. No.: WO2021/071150
PCT Pub. Date: Apr. 15, 2021

(65) Prior Publication Data
US 2024/0024123 A1    Jan. 25, 2024

(30) Foreign Application Priority Data
Oct. 7, 2019   (KR) ........................ 10-2019-0124087

(51) Int. Cl.
*A61F 2/44*       (2006.01)
*A61F 2/30*       (2006.01)

(52) U.S. Cl.
CPC ........ *A61F 2/4455* (2013.01); *A61F 2/30771* (2013.01); *A61F 2002/30405* (2013.01);
(Continued)

(58) Field of Classification Search
CPC .......... A61F 2/4455; A61F 2/442; A61F 2/44; A61F 2/4405; A61F 2/4425; A61F 2/443
See application file for complete search history.

(56) References Cited

U.S. PATENT DOCUMENTS 8,388,686 B2 *   3/2013   Aebi .................... A61F 2/4425
                                                    623/17.15
9,034,045 B2 *   5/2015   Davenport ............ A61F 2/4465
                                                    623/17.11
(Continued)

FOREIGN PATENT DOCUMENTS

CN        103501734 A     1/2014
CN        206007347 U     3/2017
(Continued)

*Primary Examiner* — Ellen C Hammond
*Assistant Examiner* — Holly Joanna Lane
(74) *Attorney, Agent, or Firm* — NKL Law; Jae Youn Kim

(57) ABSTRACT

The present disclosure relates to an intervertebral fusion cage configured to be inserted between vertebral bodies in a lowest state and improving fixation by bone screws inserted through end plates. The intervertebral fusion cage of the present disclosure may replace intervertebral fusion cages having heights within a given range. Therefore, manufacturers may reduce the number of product groups and the amount of inventory. In addition, because the height of the intervertebral fusion cage of the present disclosure is linearly adjustable according to the distance between vertebral bodies of patients unlike conventional intervertebral fusion cages having heights preset at predetermined intervals, surgery may be performed at an optimal height according to the conditions of patients.

14 Claims, 23 Drawing Sheets

(52) U.S. Cl.
CPC .............. *A61F 2002/30784* (2013.01); *A61F 2250/0004* (2013.01)

(56) References Cited

U.S. PATENT DOCUMENTS

| | | | |
|---|---|---|---|
| 9,561,116 B2* | 2/2017 | Weiman | .................. A61F 2/447 |
| 9,585,762 B2 | 3/2017 | Suddaby et al. | |
| 9,962,272 B1 | 5/2018 | Daffinson et al. | |
| 11,285,014 B1* | 3/2022 | Josse | ..................... A61F 2/4455 |
| 11,857,432 B2* | 1/2024 | Keller | ..................... A61F 2/447 |
| 2014/0277487 A1 | 9/2014 | Davenport et al. | |
| 2017/0172756 A1* | 6/2017 | Faulhaber | ................ A61F 2/447 |
| 2017/0224505 A1* | 8/2017 | Butler | ....................... A61F 2/44 |
| 2018/0193160 A1 | 7/2018 | Hsu et al. | |
| 2019/0038435 A1 | 2/2019 | Daffinson et al. | |
| 2019/0133782 A1 | 5/2019 | McLaughlin et al. | |
| 2019/0254838 A1* | 8/2019 | Miller | .................. A61F 2/4455 |
| 2021/0322181 A1* | 10/2021 | Predick | ................. A61F 2/4425 |
| 2022/0387184 A1* | 12/2022 | Josse | .................. A61F 2/30749 |

FOREIGN PATENT DOCUMENTS

| | | |
|---|---|---|
| KR | 20130082281 A | 7/2013 |
| KR | 10-2014-0009453 A | 1/2014 |
| KR | 10-1692567 B1 | 1/2017 |
| KR | 10-2147077 B1 | 8/2020 |
| WO | 2010121028 A2 | 10/2010 |
| WO | 2012121726 A1 | 9/2012 |
| WO | 2018208070 A1 | 11/2018 |

* cited by examiner

HEIGHT-ADJUSTABLE INTERVERTEBRAL FUSION CAGE

TECHNICAL FIELD

The present disclosure relates to a height-adjustable intervertebral fusion cage, and more particularly, to an intervertebral fusion cage that is configured to be inserted between vertebral bodies while having the lowest height thereof and improve fixation by bone screws inserted through end plates.

BACKGROUND ART

The vertebral column includes 32 to 35 vertebrae and intervertebral disks, which are simply called disks, and is the central part of the body that connects the skull at the top and the pelvis at the bottom.

The vertebral column is composed of 7 cervical vertebrae, 12 thoracic vertebrae, 5 lumbar vertebrae, 5 sacral vertebrae (sacrum), and 3 to 5 coccygeal vertebrae (coccyx). In adults, the five sacral vertebrae fuse into one sacrum, and the three to five coccygeal vertebrae fuse into one coccyx.

Intervertebral fusion (interbody fusion) is a method of treating serious spinal diseases that last for a long time. In interbody fusion surgery, an intervertebral disk (disk) is removed, and a cage is inserted as a substitute between adjacent vertebral bodies to join the adjacent vertebral bodies together.

Interbody fusion methods for the lumbar spine may be classified, depending on the insertion direction of a cage, into posterior lumbar interbody fusion (PLIF), transforaminal lumbar interbody fusion (TLIF), lateral lumbar interbody fusion (LLIF), oblique lumbar interbody fusion (OLIF), anterior lumbar interbody fusion (ALIF), etc.

Posterior lumbar interbody fusion (PLIF) is a method of making an incision along the midline of the lumbar spine to entirely expose a vertebra, removing a posterior portion of the vertebra, removing a disk, and inserting PLIF cages.

Posterior lumbar interbody fusion (PLIF) is the oldest method among lumbar interbody fusion methods, and is necessary when fusing two or three vertebrae together. However, posterior lumbar interbody fusion (PLIF) has disadvantages such as a high possibility of adhesions at the nerves, ligaments, and muscles due to surgical procedures, a long recovery time due to a large incision area, and serious sequelae in some patients.

PLIF cages, a pair of small cages configured to be arranged at the left and right sides, are smallest among all the cages used for interbody fusion.

Transforaminal lumbar interbody fusion (TLIF) is a surgical method in which small incisions are made along both sides of a spine muscle to minimally expose the body of a vertebra, and then while removing a portion of the vertebra to expose a neural foramen, a TLIF cage is inserted instead of a disk. This surgical technique is advantageous in terms of less bleeding and a short operation time and is suitable for one joint, but PLIF is required when treating multiple sites. Most TLIF cages are arc-shaped, and thus the convex portion of a TLIF cage is oriented toward the abdomen by inserting and rotating the TLIF cage between vertebral bodies. TLIF cages are larger than PLIF cages, but the supporting areas of TLIF cages are smaller than those of LLIF cages or ALIF cages, which will be mentioned later.

Anterior lumbar interbody fusion (ALIF) has several advantages, such as quick recovery from surgery and a low possibility of adhesions. However, ALIF requires a highly advanced skill in making an incision in the anterior (abdomen) and accessing the spine while dislodging the internal organs. ALIF cages have an advantage of having the largest support areas among all interbody fusion cages.

As such an ALIF cage, a self-supporting cage (integrated cage) having holes through which screws can be inserted and fixed to vertebral bodies to prevent separation of the cage after surgery is disclosed (US 2014-0277487 A).

In addition, U.S. Pat. No. 9,585,762 and US 2019-0133782 A disclose height-adjustable, self-supporting ALIF cages. In U.S. Pat. No. 9,585,762, a vertical ratchet 302 is used for height adjustment. That, angle adjustment is substantially performed instead of height adjustment. US 2019-0133782 A discloses height adjustment but has problems such as a very complicated structure and difficulty in manufacturing.

PRIOR ART DOCUMENTS

Patent Documents (PATENT DOCUMENT 1) U.S. Pat. No. 9,585,762 B2
(PATENT DOCUMENT 2) US 2019-0133782 A
(PATENT DOCUMENT 3) US 2014-0277487 A

DESCRIPTION OF EMBODIMENTS

Technical Problem

An objective of the present disclosure for solving the problems described above is to provide an intervertebral fusion cage, which is insertable between vertebral bodies in a lowest state, adjustable in height in the inserted state, capably of stably supporting the movement of a pair of end plates, and particularly capably of improving fixation owing to bone screws inserted through the end plates.

Solution to Problem

To achieve the objective, the present disclosure provides an intervertebral fusion cage including: a first end plate and a second end plate, which are configured to be in contact with adjacent vertebral bodies; a distal movable block fixed in a state in which the distal movable block is movable relative to a plate slope portion formed on an end of the first end plate and a plate slope portion formed on an end of the second end plate; a proximal movable block fixed in a state in which the proximal movable block is movable relative to a plate slope portion formed on another end of the first end plate and a plate slope portion formed on another end of the second end plate; an adjustment member rotatably fixed to the proximal movable block and screwed to the distal movable block to adjust a distance between the distal movable block and the proximal movable block; a first guide portion formed on the first end plate toward the second end plate; a second guide portion formed on the second end plate toward the first end plate to limit, by sliding between the first guide portion and the second guide portion, a movement direction in which the first end plate and the second end plate are moved close to or away from each other; a bone screw configured to be inserted into bone screw holes formed in the first end plate and the second end plate; and a locking member configured to be fastened to the proximal movable block to prevent separation of the bone screw, wherein the first guide portion and the second guide portion support a load in a length or width direction of the first end plate and the second end plate.

Block sliders are formed on the distal movable block and the proximal movable block, and plate sliders slidable with respect to the block sliders are formed on the plate slope portions.

In addition, the block sliders of the distal movable block are arranged on both sides of block slope portions corresponding to the plate slope portions, auxiliary block sliders are arranged on outer sides of the block sliders, and auxiliary plate sliders corresponding to the auxiliary block sliders are formed on the first end plate and the second end plate.

In addition, reinforcing slope portions are formed on center portions of the block slope portions, and reinforcing slope portion seats corresponding to the reinforcing slope portions are formed on the first and second end plates.

In addition, the adjustment member includes: a threaded portion formed on an end thereof and configured to be screwed to the distal movable block; and an adjustment member support surface formed on another end thereof and rotatable at a given position with respect to the proximal movable block.

In addition, the first guide portion includes a pillar protruding toward the second end plate, and the second guide portion includes an extension wall protruding toward the first end plate and slidable with respect to the pillar.

In addition, an accommodation portion is formed near the pillar to receive the extension wall when the first end plate and the second end plate are moved close to each other.

In addition, a guide recess is formed in the extension wall to guide insertion of the pillar.

In addition, a clearance cut portion is formed on the extension wall to prevent interference with the bone screw.

In addition, the locking member includes a locking plate configured to cover the bone screw and a locking bolt configured to be fixed to the proximal movable block through the locking plate, and a locking-bolt coupling portion is formed on the proximal movable block such that the locking bolt is coupled to a front end of the adjustment member.

In addition, a locking protrusion protruding toward the bone screw is formed on a rear end of the locking plate.

In addition, when the locking bolt is coupled, the locking bolt comes into contact with the adjustment member and pushes the adjustment member.

In addition, an anchor portion having no screw thread is formed on a distal end portion of the bone screw.

In addition, the anchor portion includes an anchor groove extending in a length direction of the bone screw.

In addition, the anchor portion includes an anchor protrusion protruding in radial directions.

Advantageous Effects of Disclosure

According to the present disclosure, cages having heights within a given range may be replaced with one cage. Therefore, manufacturers may reduce the number of product groups and the amount of inventory. In addition, because the height of the cage of the present disclosure is linearly adjustable according to the distance between vertebral bodies of patients unlike conventional intervertebral fusion cages having heights preset at predetermined intervals, surgery may be performed at an optimal height according to the conditions of patients.

In addition, because the cage is insertable in a lowest state, it is not necessary to fabricate additional test inserts according to a proper intervertebral spacing, and surgeons are not needed to sequentially insert a plurality of inserts for securing an insertion space.

MODE OF DISCLOSURE

Figure 1:
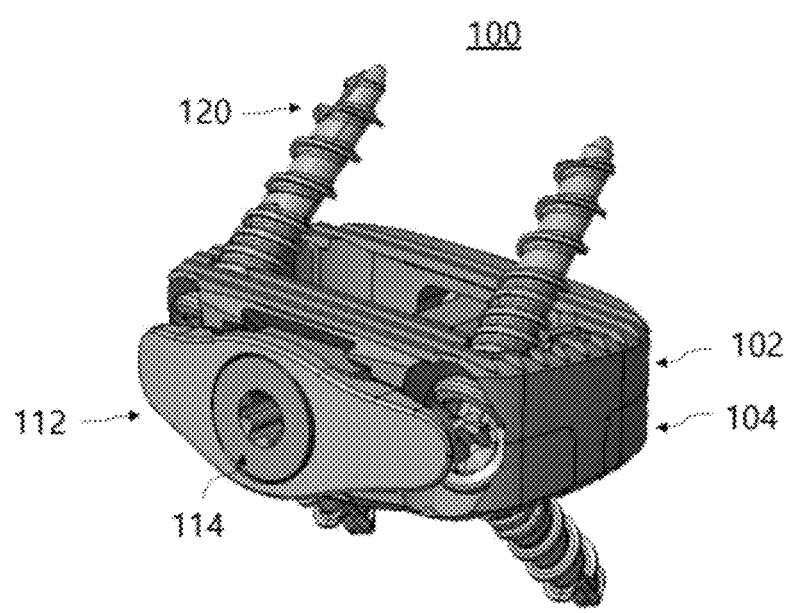
FIG. 1 is an upper-front perspective view illustrating an intervertebral fusion cage in a lowest state according to an embodiment of the present disclosure.
Figure 2:
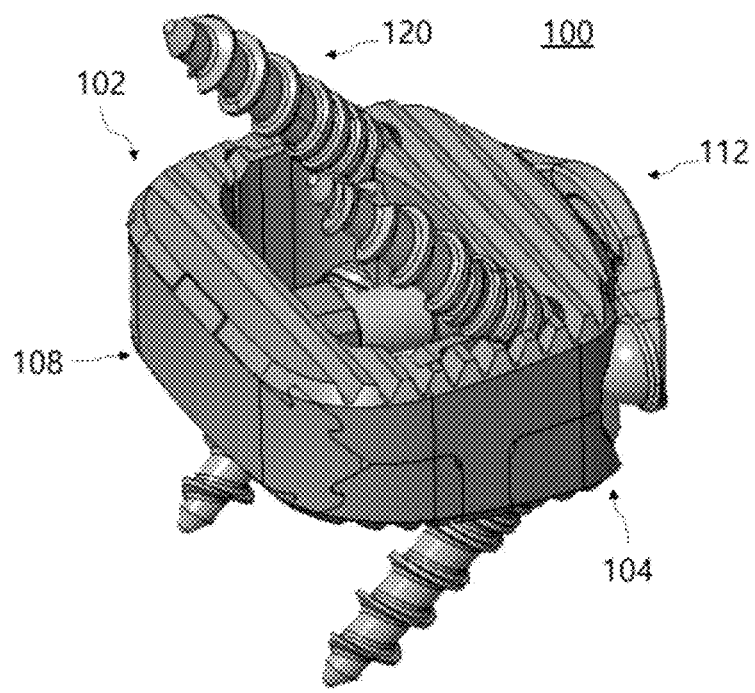
FIG. 2 is an upper-rear perspective view illustrating the intervertebral fusion cage shown in FIG. 1.
Figure 3:
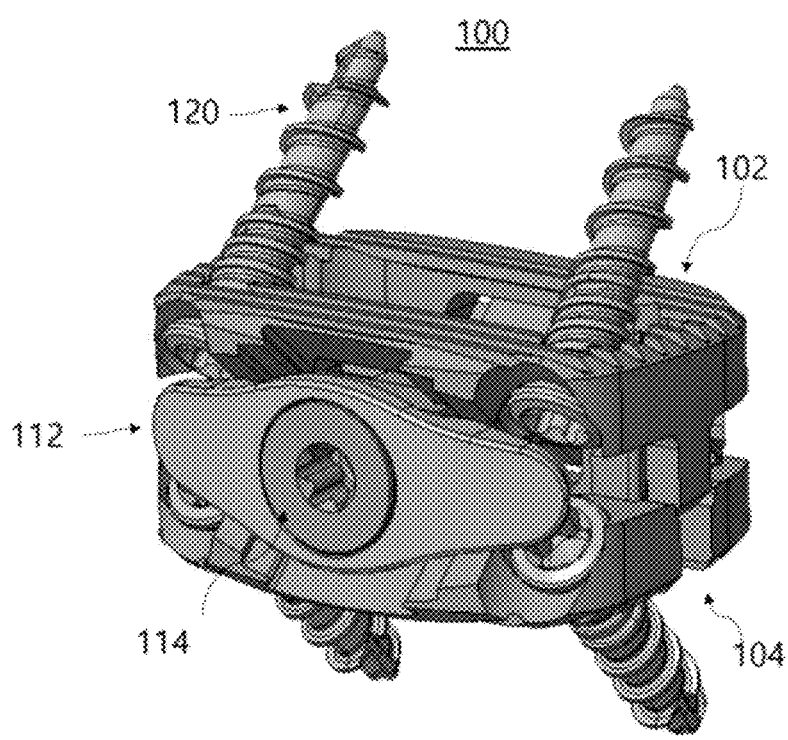
FIG. 3 is an upper-front perspective view illustrating the intervertebral fusion cage in a highest state according to an embodiment.
Figure 4:
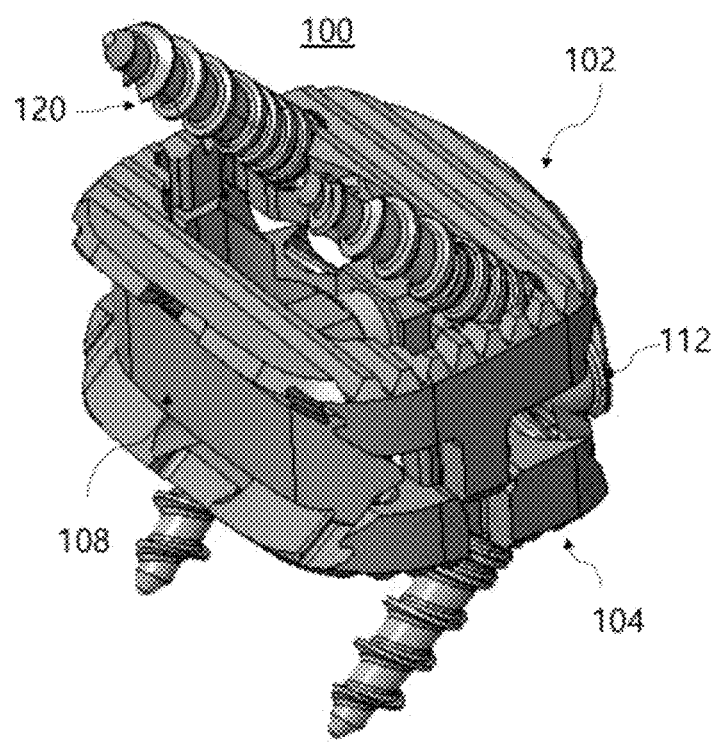
FIG. 4 is an upper-rear perspective view illustrating the intervertebral fusion cage shown in FIG. 3.
Figure 5:
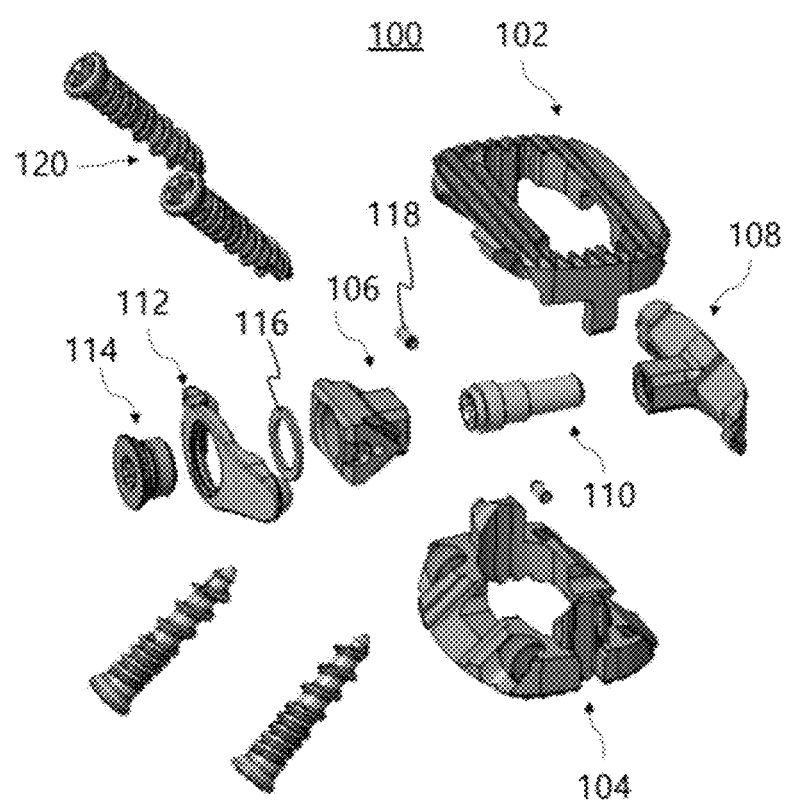
FIG. 5 is an exploded upper-front perspective view illustrating the intervertebral fusion cage according to an embodiment.
Figure 6:
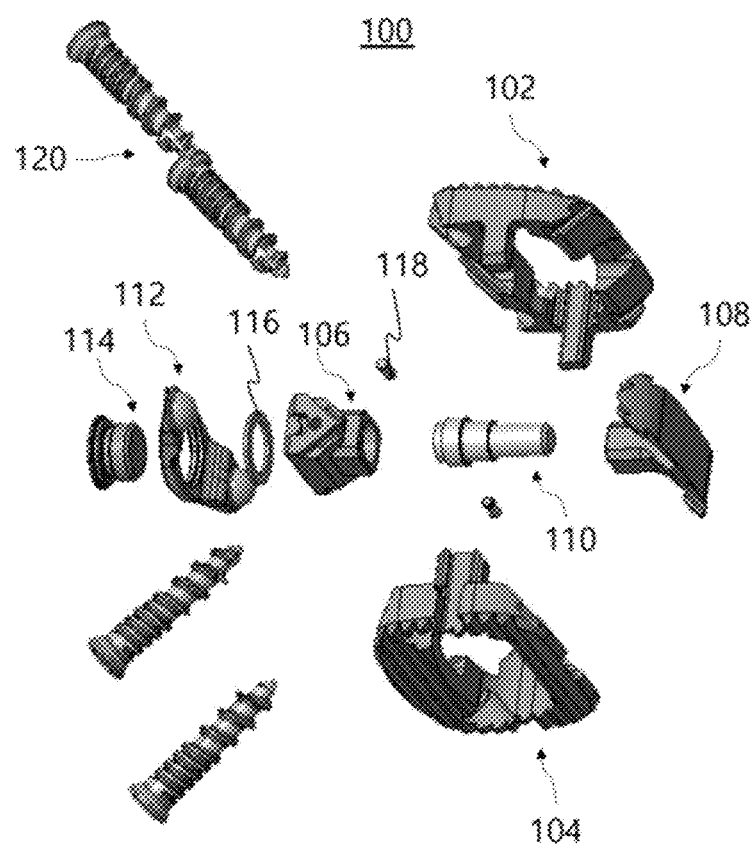
FIG. 6 is an exploded upper-rear perspective view illustrating the intervertebral fusion cage according to an embodiment.
Figure 7:
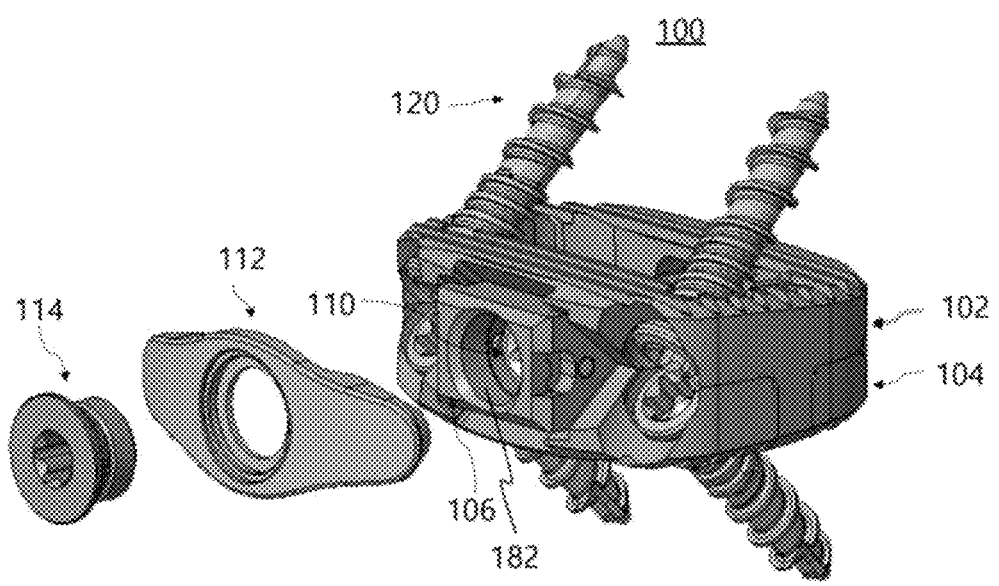
FIG. 7 is a perspective view illustrating coupling of a locking plate to the intervertebral fusion cage according to an embodiment.

Hereinafter, preferred embodiments of the present disclosure will be described with reference to the accompanying drawings. In the drawings, the same elements may be denoted with the same reference numerals even though the elements are shown in different drawings, and detailed descriptions related to well-known functions or configurations will be ruled out in order not to unnecessarily obscure subject matters of the present disclosure.

FIGS. 1 to 7 entirely illustrate an intervertebral fusion cage 100 according to embodiments, and FIGS. 8 to 23 illustrate elements of the intervertebral fusion cage 100.

The intervertebral fusion cage 100 generally includes: a first end plate 102 and a second end plate 104, which face each other in a vertical direction; a distal movable block 108 and a proximal movable block 106, which are arranged between the first end plate 102 and the second end plate 104 and movable according to the distance between the first end plate 102 and the second end plate 104; an adjustment member 110, which is connected to the distal movable block 108 through the proximal movable block 106; bone screws 120, which are inserted into the first end plate 102 and the second end plate 104 for being fixed to vertebral bodies; and a locking member configured to prevent separation of the bone screws 120.

The first end plate 102 and the second end plate 104 include a first plate body 122 and a second plate body 146, which have tooth-shaped protrusions on surfaces to be brought into contact with vertebral bodies. The tooth-shaped protrusions are formed to prevent separation from vertebral bodies and may be variously modified. In addition, a first window 145 and a second window 172 may be respectively formed in a center portion of the first plate body 104 and a center portion of the second plate body 146 such that a bone graft may be inserted therethrough.

Figure 8:
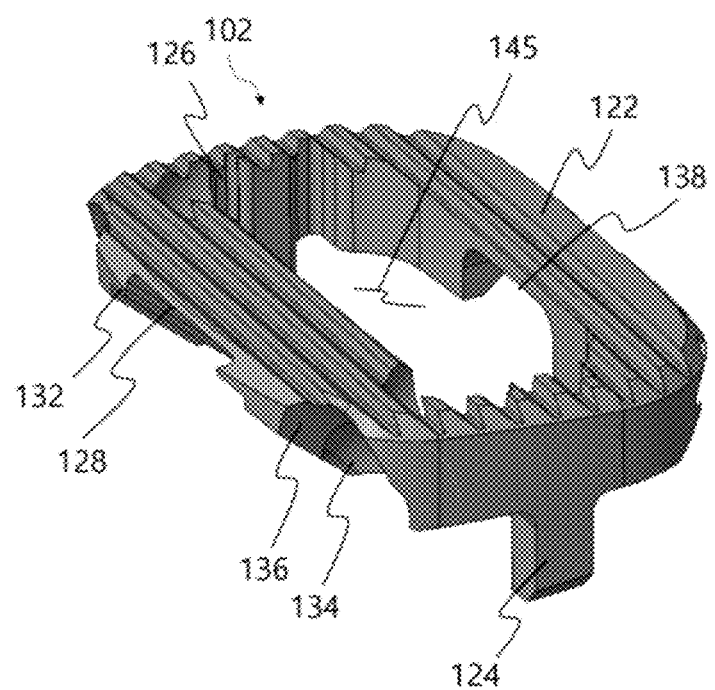
FIG. 8 is an upper-front perspective view illustrating a first end plate according to an embodiment.
Figure 9:
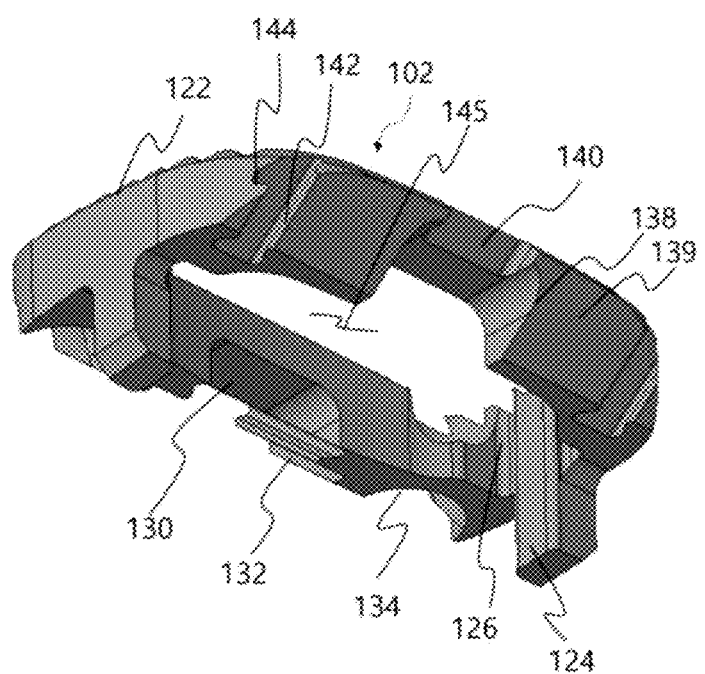
FIG. 9 is a rear-lower perspective view illustrating the first end plate shown in FIG. 8

In addition, as shown in FIGS. 8 and 9, a proximal movable block seat 130 is formed in the length direction of the first plate body 122 toward the center of the body, and a distal movable block seat 138 is formed in the length direction of the first plate body 122 away from the center of the body. A plate slope portion 128 extends from the proximal movable block seat 130, and a pair of plate sliders 132 facing each other are formed on both sides of the plate slope portion 128. In addition, bone screw holes 134 are formed on outer sides of the plate sliders 132. The bone screw holes 134 are penetration holes into which the bone screws 120 may be inserted, and guide surfaces 136 for guiding the bone screws 120 may be formed on entrance sides of the bone screw holes 134. In addition, plate slope portions 139 are formed around the distal movable block seat 138. The plate slope portions 139 are formed on both ends of the distal movable block seat 138, and plate sliders 142 are respectively formed on outer sides of the plate slope portions 139. In addition, auxiliary plate sliders 144 facing the plate sliders 142 may be formed on outer sides of the plate sliders 142. The plate sliders 132 proximal to the center of the body and the plate sliders 142 distal to the center of the body are sloped are sloped in a manner such that the plate sliders 132 and the plate sliders 142 approach the center of the first plate body 122 as it goes away from a surface of the first plate body 122 in the thickness direction of the first plate body 122.

In addition, a reinforcing slope portion seat 140 extends from the distal movable block seat 138. A reinforcing slope portion 200, which is described later, may be positioned on the reinforcing slope portion seat 140, and when the distal movable block 108 is moved, the reinforcing slope portion 200 may not interfere with the first plate body 122 owing to the reinforcing slope portion seat 140.

Figure 10:
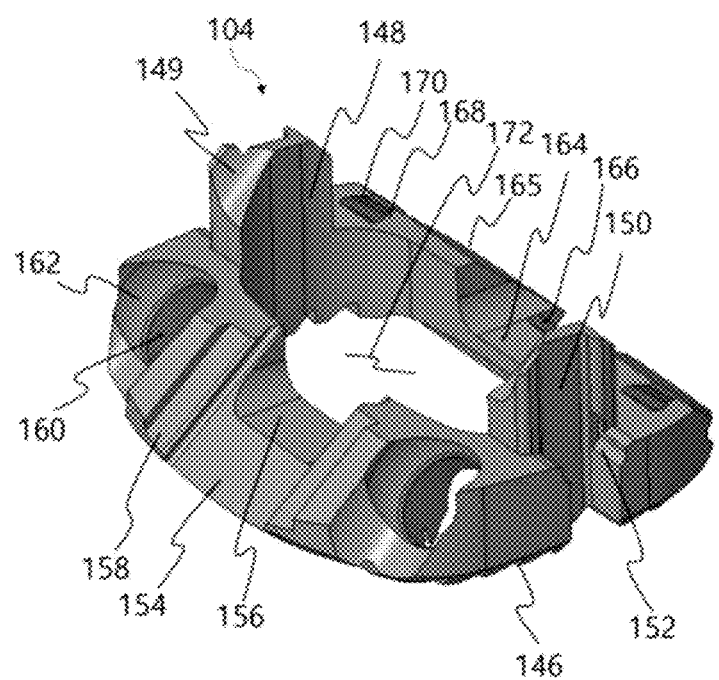
FIG. 10 is a upper-front perspective view illustrating a second end plate according to an embodiment.
Figure 11:
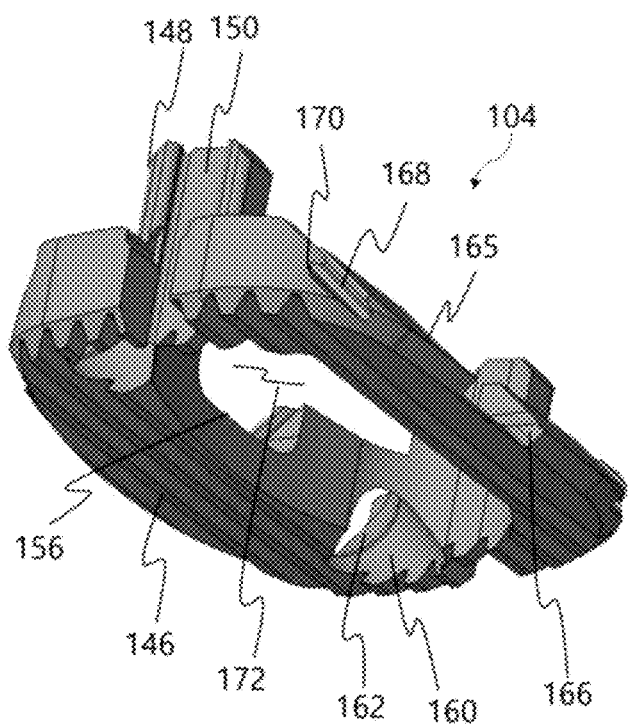
FIG. 11 is a rear-lower perspective view illustrating the second end plate shown in FIG. 10.

Similarly, as shown in FIGS. 10 and 11, a proximal movable block seat 156 is formed in the length direction of the second plate body 146 toward the center of the body, and a distal movable block seat 164 is formed in the length direction of the second plate body 146 away from the center of the body. A plate slope portion 154 extends from the proximal movable block seat 156, and a pair of plate sliders 158 facing each other are formed on both sides of the plate slope portion 154. In addition, bone screw holes 160 are formed in outer sides of the plate sliders 158. The bone screw holes 160 are penetration holes into which the bone screws 120 may be inserted, and guide surfaces 162 for guiding the bone screws 120 may be formed on entrance sides of the bone screw holes 160. In addition, plate slope portions 165 are formed around the distal movable block seat 164. The plate slope portions 165 are formed on both ends of the distal movable block seat 164, and plate sliders 168 are respectively formed on outer sides of the plate slope portions 165. In addition, auxiliary plate sliders 170 facing the plate sliders 168 are formed on outer sides of the plate sliders 168. The plate sliders 158 proximal the center of the body and the plate sliders 168 distal to the center of the body are sloped in a manner such that the plate sliders 158 and the plate sliders 168 approach the center of the second plate body 146 as it goes away from a surface of the second plate body 146 in the thickness direction of the second plate body 146.

In addition, a reinforcing slope portion seat 166 extends from the distal movable block seat 164. A reinforcing slope portion 200, which is described later, may be positioned on the reinforcing slope portion seat 166, and when the distal movable block 108 is moved, the reinforcing slope portion 200 may not interfere with the second plate body 146 owing to the reinforcing slope portion seat 166.

Figure 12:
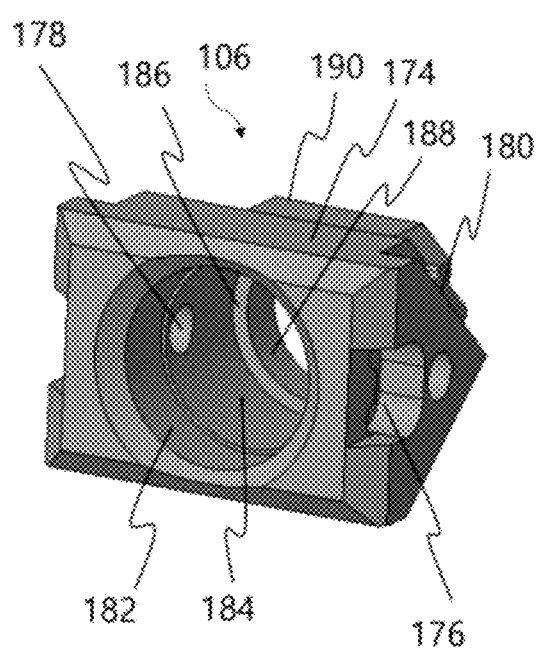
FIG. 12 is an upper-front perspective view illustrating a proximal movable block according to an embodiment.
Figure 13:
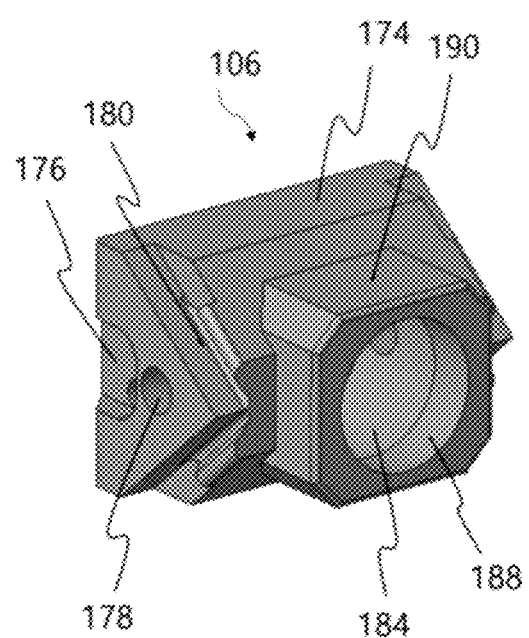
FIG. 13 is an upper-rear perspective view illustrating the proximal movable block shown in FIG. 12.

As shown in FIGS. 12 and 13, block slope portions 174 are formed on the proximal movable block 106 around a proximal connection tube body 190 having an adjustment member hole 188 into which the adjustment member 110 is to be inserted and supported. Block sliders 180, which are to be slidably coupled to the plate sliders 132 and 158 formed on the first and second end plates 102 and 104, are arranged on both sides of the block slope portions 174. The adjustment member hole 188 includes: a support portion 184 that is to be in contact with the adjustment member 110 for supporting the adjustment member 110; and a support jaw 186 formed on a distal end side of the support portion 184 to prevent separation of the adjustment member 110. In addition, pinholes 178 are formed in lateral portions of the proximal movable block 106 to prevent the adjustment member 110 from being separated toward the center of the body. In addition, tool seats 176 are formed in the lateral portions of the proximal movable block 106 to fix the intervertebral fusion cage 100 using a tool. In addition, a locking-bolt coupling portion 182, to which a locking bolt 114 (described later) is to be coupled, is formed in a region that is more proximal than a region in which the adjustment member 110 is to be inserted.

Figure 14:
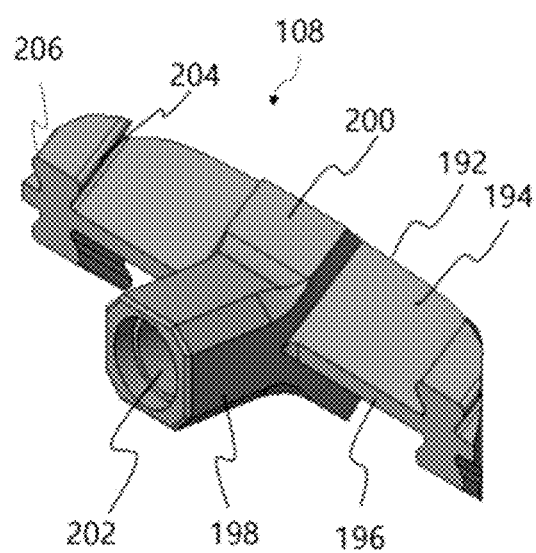
FIG. 14 is an upper-front perspective view illustrating a distal movable block according to an embodiment.
Figure 15:
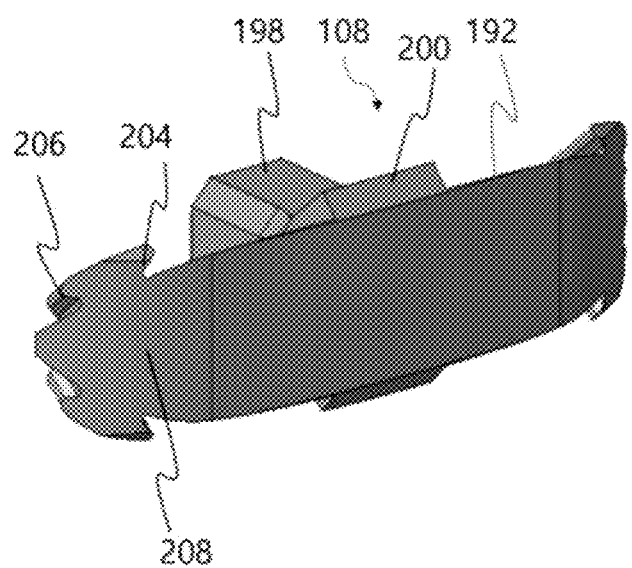
FIG. 15 is an upper-rear perspective view illustrating the distal movable block shown in FIG. 14.

As shown in FIGS. 14 and 15, a distal connection tube body 198 having a movable block thread portion 202 to which the adjustment member 110 is to be screwed is formed on a center portion of the distal movable block 108, and wing portions 196 are provided on both sides of the distal connection tube body 198. Block slope portions 194 are formed on the wing portions 196, and block sliders 204 are arranged on both sides of the wing portions 196. Auxiliary block sliders 206 are formed on outer sides of the block sliders 204. The block sliders 204 and the auxiliary block sliders 206 are configured to be slidably coupled to the plate sliders 142 and 168 and the auxiliary plate sliders 144 and 170 of the first and second end plates 102 and 104, respectively.

The distal movable block 108 has a distal wall 192 for ease of insertion between vertebral bodies, and the distal wall 192 is formed in one piece with the block slope portions 194. Furthermore, in a lowest state, the distal wall 192 is in contact with an end portion of the first end plate 102 and an end portion of the second end plate 104, forming an insertion portion as a whole. In particular, distal bent surfaces 208 are formed on both sides of the distal wall 192, further facilitating insertion.

Reinforcing slope portions 200 are formed in a center region of the distal movable block 108 to reinforce the distal movable block 108 when the block sliders 204 and the auxiliary block sliders 206 support a load. As described above, the reinforcing slope portions 200 are stably positioned while being inserted into the reinforcing slope portion seats 140 and 166 of the first end plate 102 and the second end plate 104.

The distal movable block 108 and the proximal movable block 106 have a substantially wedge-shaped structure, and are configured to push or support the first end plate 102 and the second end plate 104 when lifting or lowering the first end plate 102 and the second end plate 104.

Figure 16:
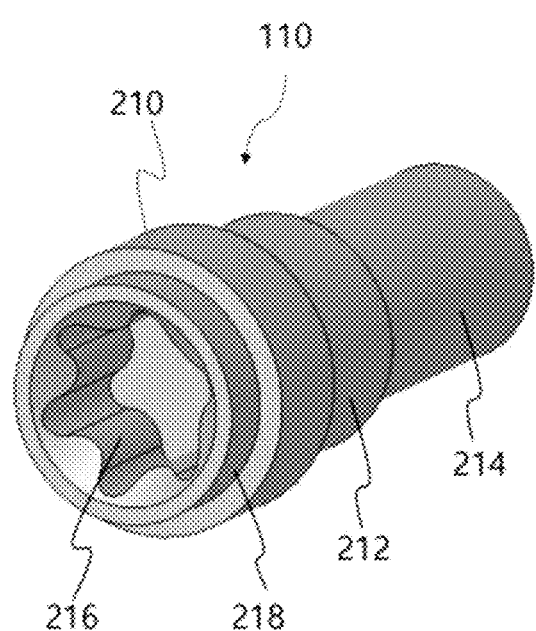
FIG. 16 is a perspective view illustrating an adjustment member according to an embodiment.

The adjustment member 110 may have a substantially bolt shape as shown in FIG. 16. That is, the adjustment member 110 has an adjustment member support surface 210 and an adjustment thread portion 214. A connection portion 212 may be formed between the adjustment member support surface 210 and the adjustment thread portion 214. A pin seat 218 may be formed on a proximal side of the adjustment member support surface 210, and a tool recess 216 may be formed in a center portion of the pin seat 218 for driving the adjustment member 110. Although the adjustment thread portion 214 is a male screw portion, a detailed shape thereof is not shown in the drawings.

The adjustment member support surface 210 is rotatably supported in contact with the support portion 184 of the distal movable block 108. The adjustment thread portion 214 is screwed to the movable block thread portion 202 of the adjustment member 110. Although the movable block thread portion 202 is a female screw portion, a detailed shape thereof is not shown in the drawings. In addition, because a distal clearance surface of the adjustment member support surface 210 is brought into contact with the support jaw 186, the adjustment member 110 is not separated from the distal movable block 108 in a distal direction. In addition, a pin member 118 is inserted into the pin seat 218 and positioned in the pin seat 218 such that the adjustment member 110 may not be separated from the distal movable block 108 in a proximal direction.

Therefore, the adjustment member 110 is rotatable at a given internal position of the adjustment member 110.

A pair of pillars 124 are formed on both sides of the first plate body 122 in a thickness direction of the first plate body 122, that is, in a direction toward the second end plate 104. In addition, accommodation portions 126 for receiving extension walls 148 (described later) are formed near the pillars 124. In addition, the extension walls 148 are formed on both sides of the second plate body 146 in a thickness direction, that is, in a direction toward the first end plate 102, and grooves 150 for receiving and guiding the pillars 124 are formed in inner sides of the extension walls 148. Therefore, as the pillars 124 are inserted into the grooves 150 and vertically moved in the grooves 150, the first end plate 102 and the second end plate 104 may be moved toward or away from each other in a restricted state. Here, the pillars 124 and the extension walls 148 correspond to a first guide portion and a second guide portion. The first guide portion and the second guide portion have a function of supporting a load or torsion in the length or width direction of the first end plate 102 and the second end plate 104.

In addition, when viewed from the top, the extension walls 148 have a substantially U-shape to surround the pillars 124. In addition, clearance cut portions 149 are formed on the extension walls 148 such that when the bone screws 120 are inserted in a narrow space, the insertion of the bone screws 120 may not be obstructed by the extension walls 148

The locking member may include: a locking plate 112 configured to cover the bone screws 120; and the locking bolt 114 configured to be fixed to the proximal movable block 106 through the locking plate 112.

Figure 17:
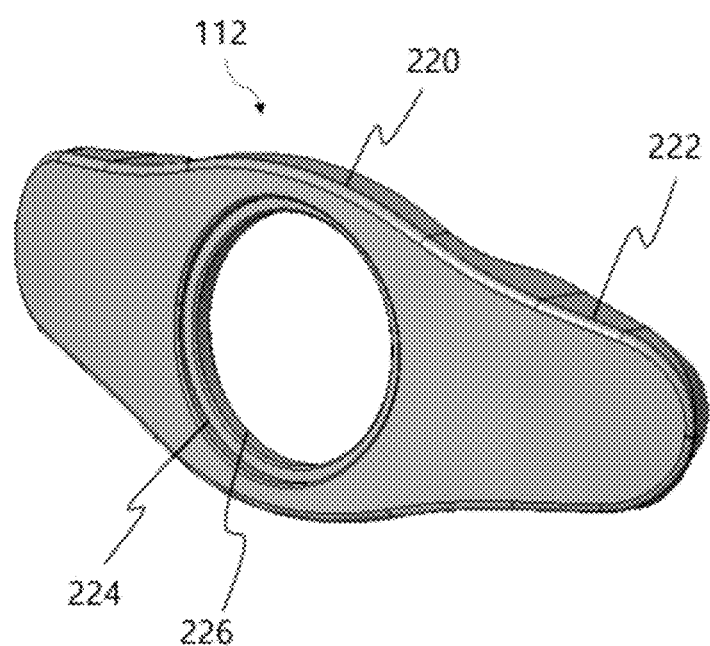
FIG. 17 is an upper-front perspective view illustrating the locking plate according to an embodiment.
Figure 18:
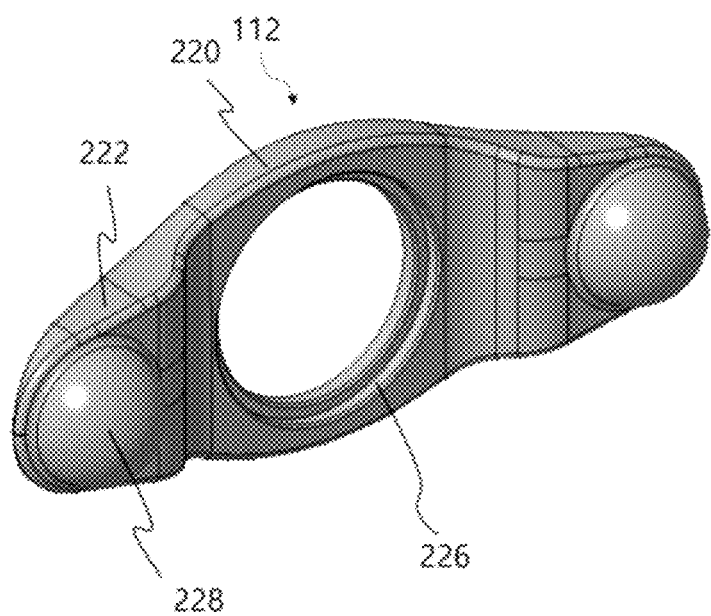
FIG. 18 is an upper-rear perspective view illustrating the locking plate shown in FIG. 17.
Figure 19:
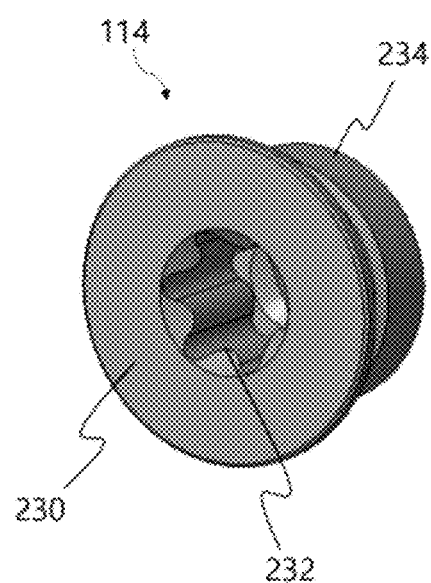
FIG. 19 is an upper-front perspective view illustrating a locking bolt according to an embodiment.

As shown in FIGS. 17 and 18, the locking plate 112 includes a locking plate body 220 shaped like a plate, and cover portions 222 extending from both sides of the locking plate body 220 may be slightly curved to cover the locking bolt 114. In addition, locking protrusions 228 may be formed on rear ends of the cover portions 222, that is, distal sides of the cover portions 222. The locking protrusions 228 may have a substantially hemispherical shape and may be variously modified. Because the distance between the first end plate 102 and the second end plate 104 is variable, the distance between screw heads 236 of the bone screws 120 inserted into the first end plate 102 and the second end plate 104 is also variable. Therefore, it is preferable that the locking protrusions 228 be formed on the cover portions 222 to cover the screw heads 236 while the distance between the first end plate 102 and the second end plate 104 varies from a minimal value to a maximum value.

In addition, a locking bolt hole 226 is formed in a center portion of the locking plate body 220 to receive a portion of the locking bolt 114. In addition, a locking bolt seat 224 may be formed around the locking bolt hole 226 to support a rear end of a locking bolt head 230 of the locking bolt 114. In addition, the locking-bolt coupling portion 182 is formed on the proximal movable block 106 such that the locking bolt 114 may be coupled to a front end of the adjustment member 110 through the locking-bolt coupling portion 182. Although the locking-bolt coupling portion 182 is a female screw portion, a detailed shape thereof is not shown in the drawings.

The locking bolt 114 includes: the locking bolt head 230 configured to be placed on the locking bolt seat 224; a locking thread portion 234 on which a thread is formed for coupling with the locking-bolt coupling portion 182; and a tool recess 232 for coupling with a tool. In particular, a ring groove may be formed in the locking bolt 114, and a fixing ring 116 may be fitted to the ring groove to prevent separation of the locking bolt 114 from the locking plate 112.

When the locking bolt 114 is fastened to the proximal movable block 106, the locking bolt 114 is brought into contact with the adjustment member 110, and thus the locking bolt 114 pushes the adjustment member 110. At this time, friction occurs between the locking bolt 114 and the adjustment member 110. As a result, friction increases in a threaded region of the adjustment member 110 such that even when a load, particularly a repetitive load, is applied to the first end plate 102 and the second end plate 104, the adjustment member 110 may not be unfastened.

Next, the bone screws 120, and bone screws 242, 252 and 264, which are modification examples of the bone screws 120, will be described according to embodiments with reference to FIGS. 20 to 23.

Figure 20:
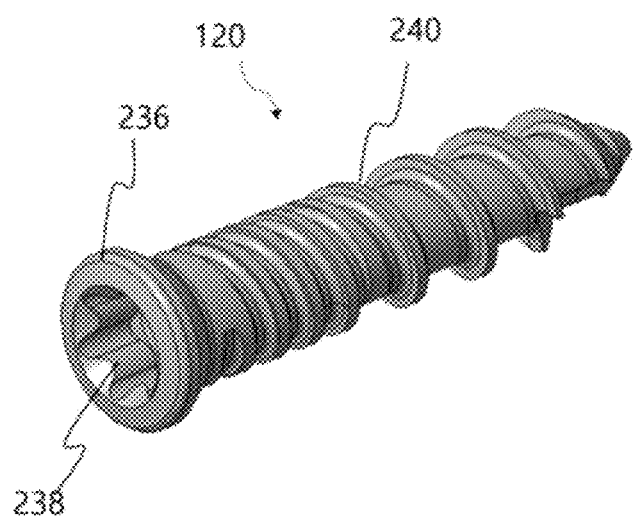
FIG. 20 illustrates a first example of a bone screw according to an embodiment.

The bone screw 120 shown in FIG. 20 may be a bone screw of the related art. The bone screw 120 includes: a screw head 236 configured to limit the degree of insertion of the bone screw 120 when the bone screw 120 is inserted into the bone screw holes 134 and 160; a tool recess 238 formed in the screw head 236 for receiving a tool; and a threaded portion 240 formed in one piece with the screw head 236 and configured to be inserted into a vertebral body. The threaded portion 240 includes a double-lead thread and a single-lead thread for both the cancellous bone and the cortical bone.

Figure 21:
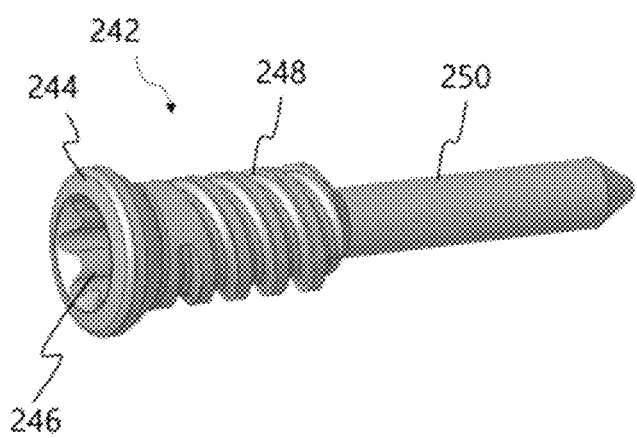
FIG. 21 illustrates a second example of the bone screw according to an embodiment.

The bone screw 242 shown in FIG. 21 includes: a screw head 244; a tool recess 246 formed in the screw head 244; and a vertebral body insertion portion, which is formed in one piece with the screw head 244 and has a proximal threaded portion 248 and a distal anchor portion 250.

A separate tool, such as an awl, is required to set an initial direction for surgery with an ALIF cage. In addition, because the fixing force of a screw fastened to cancellous bone is not great, a screw thread may often be meaningless for cancellous bone. Therefore, the bone screw 242 includes the anchor portion 250 formed on a distal end portion of the threaded portion 248. In this case, a separate tool is not necessary for setting an initial direction, and discomfort caused by screwing may be reduced because insertion is carried out by hitting.

The anchor part 250 of the bone screw 242 has a nail-like shape in which only an end portion of a shank has a conical tip for ease of insertion.

Figure 22:
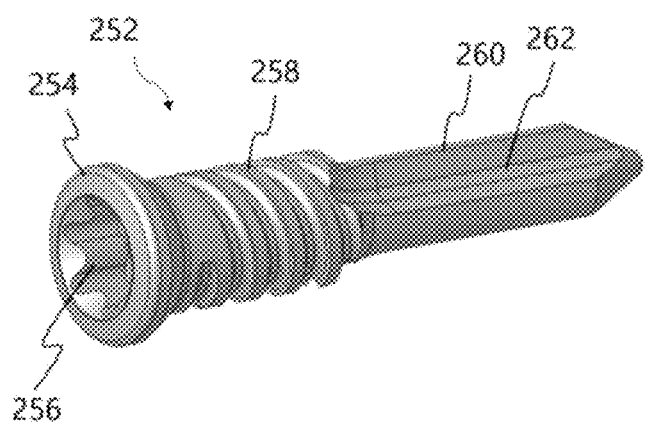
FIG. 22 is a third example of the bone screw according to an embodiment.

The bone screw 252 shown in FIG. 22 includes: a screw head 254, a tool recess 256 formed in the screw head 254; and a vertebral body insertion portion, which is formed in one piece with the screw head 254 and has a proximal threaded portion 258 and a distal anchor portion 260. In addition, an anchor groove 262 is formed in the anchor portion 260.

The anchor groove 262 is formed in the length direction of the bone screw 252 to increase anchoring force by increasing a contact area with bone.

Figure 23:
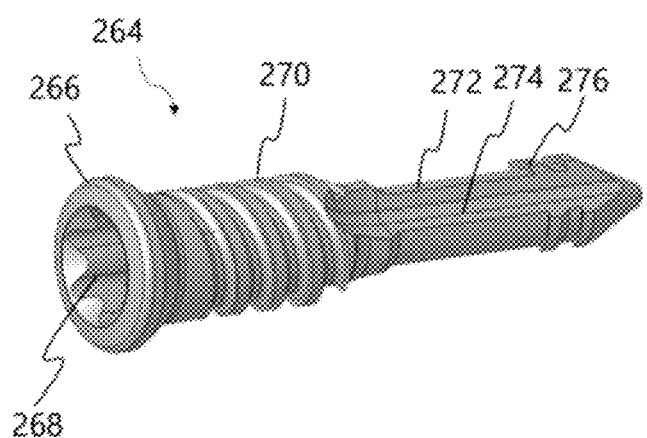
FIG. 23 is a fourth example of the bone screw according to an embodiment.

The bone screw 264 shown in FIG. 23 includes: a screw head 266; a tool recess 268 formed in the screw head 266; and a vertebral body insertion portion, which is formed in one piece with the screw head 268 and has a proximal threaded portion 270 and a distal anchor portion 272. In addition, an anchor groove 274 is formed in the anchor portion 272, and an anchor protrusion 276 protruding in radial directions is formed on the anchor portion 272.

The anchor groove 274 is formed in the length direction of the bone screw 252 to increase anchoring force by increasing a contact area with bone, and along with this, the anchor protrusion 276 prevents separation of the bone screw 264.

The intervertebral fusion cage 100 is configured as described above, and a surgery method using the intervertebral fusion cage 100 will now be described.

First, a surgical path to vertebral bodies is secured using surgical tools, and a disk is removed. Then, in a state in which the intervertebral fusion cage 100 is held by a cage holder (not shown), the intervertebral fusion cage 100 is inserted between the vertebral bodies from which the disk has been removed.

Thereafter, the proximal movable block 106 and the distal movable block 108 are moved close to each other by inserting a tool such as a screwdriver into the tool recess 216 of the adjustment member 110 and rotating the tool in one direction, and thus the first end plate 102 and the second end plate 104 are moved apart from each other.

Thereafter, the bone screws 120 are inserted into and fixed to the bone screw holes 134 and 160 of the first end plate 102 and the second end plate 104. In this case, for the insertion of the bone screws 120, holes are initially formed using a tool called an awl, and the holes are deepened with a drill. Thereafter, screw threads slightly smaller than the screw threads of the bone screws 120 are formed with a tool called a tapper to form paths for the screw threads of the bone screws 120, and then the bone screws 120 are inserted by rotating the bone screws 120 with a tool such as a screwdriver. The formation of the screw threads by the tapper may be omitted.

However, the bone screws 242, 252, and 264 shown in FIGS. 21 to 23 do not require tools such as an awl, a drill, and a tapper, but the initial orientation and insertion of the bone screws 242, 252, and 264 are performed by hitting with a tool such as a mallet. Then, the threaded portions of the bone screws 242, 252, and 264 are inserted by rotating the bone screws 242, 252, and 264 with a tool such as a screwdriver.

After the bone screws 120, 242, 252, or 264 are inserted as described above, the locking plate 112 is moved close to the proximal movable block 106, and the locking bolt 114 is coupled to the locking-bolt coupling portion 182 of the proximal movable block 106 by rotating the locking bolt 114 with a tool such as a screwdriver, thereby completing the insertion of the intervertebral fusion cage 100.

Similarly, when the intervertebral fusion cage 100 is incorrectly inserted or removed for a reoperation, the locking bolt 114 is reversely rotated with a tool such as a screwdriver, and the locking plate 112 is separated from the proximal movable block 106. Then, the bone screws 120, 242, 252, or 264 are rotated with a tool such as a screwdriver to separate the bone screws 120, 242, 252, or 264 from the intervertebral fusion cage 100. In this case, the bone screws 242, 252, or 264 having anchor portions may be separated from the intervertebral fusion cage 100 by unfastening the threaded portions of the bone screws 242, 252, or 264 and then pulling the bone screws 242, 252, or 264 with a tool such as an awl.

Thereafter, in a state in which the intervertebral fusion cage 100 is held using a cage holder (not shown), the proximal movable block 106 and the distal movable block 108 are moved away from each other by inserting a tool such as a screwdriver into the adjustment member 110 and reversely rotating the tool. Then, the first end plate 102 and the first plate body 104 are moved close to each other, and thus the height of the intervertebral fusion cage 100 is reduced. Thereafter, the intervertebral fusion cage 100 is removed from the vertebral bodies.

While preferred embodiments of the present disclosure have been described, as described above, it will be understood by those of ordinary skill in the art that various changes in form and details may be made therein without departing from the spirit and scope of the present disclosure as defined by the following claims.

INDUSTRIAL APPLICABILITY

According to the present disclosure, only one cage may be used for a given height range, thereby reducing inventory and production, and repetitive tasks and burdens on surgeons during surgery. In addition, the operation time and the amount of bleeding may be reduced, and thus the recovery time of patients may be greatly reduced. Therefore, the present disclosure may be widely used in related fields.

| {EXPLANATION OF REFERENCE NUMERALS DESIGNATING THE MAJOR ELEMENTS OF THE DRAWINGS} ||
|---|---|
| 100: intervertebral fusion cage | 102: first end plate |
| 104: second end plate | 106: proximal movable block |
| 108: distal movable block | 110: adjust member |
| 112: locking plate | 114: locking bolt |
| 116: fixing ring | 118: pin member |
| 120, 242, 252, 264: bone screws | 122: first plate body |
| 124: pillar | 126: accommodation recess |
| 128, 139, 154, 165: plate slope portions | 130, 156: proximal movable block seats |
| 132, 142, 158, 168: plate sliders | 134, 160: bone screw holes |
| 136, 162: guide surfaces | 138, 164: distal movable block seats |
| 140, 166: reinforcing slope portion seats | 144, 170: auxiliary plate sliders |
| 145: first window | 146: second plate body |
| 148: extension wall | 150: groove |
| 152: guide recess | 154: cut portion |
| 172: second window | 174, 194: block slope portion |
| 176: tool seat | 178: pinhole |
| 180, 204: block sliders | 182: locking-bolt coupling portion |
| 184: support portion | 186: support jaw |
| 188: adjustment member hole | 190: proximal connection tube body |
| 192: distal wall | 196: wing portion |
| 198: distal connection tube body | 200: reinforcing slope portion |
| 202: movable block thread portion | 206: auxiliary block slider |
| 208: distal bent surface | 210: adjustment member support surface |
| 212: connection portion | 214: adjustment thread portion |
| 216, 232, 238, 246, 256, 268: tool recesses | 218: pin seat |
| 220: locking plate body | 222: cover portion |
| 224: locking bolt seat | 226: locking bolt hole |
| 228: locking protrusion | 230: bolt head |
| 234: locking thread portion | 236, 244, 254, 266: screw heads |
| 240, 248, 258, 270: threaded portions | 250, 260, 272: anchor portions |
| 262, 274: anchor grooves | 276: anchor protrusion |

The invention claimed is:

1. An intervertebral fusion cage comprising:
a first end plate and a second end plate, which are configured to be in contact with adjacent vertebral bodies;
a distal movable block fixed in a state in which the distal movable block is movable relative to a first distal plate slope portion formed on an end of the first end plate and a second distal plate slope portion formed on an end of the second end plate;
a proximal movable block fixed in a state in which the proximal movable block is movable relative to a first proximal plate slope portion formed on another end of the first end plate and a second proximal plate slope portion formed on another end of the second end plate;
an adjustment member rotatably fixed to the proximal movable block and screwed to the distal movable block to adjust a distance between the distal movable block and the proximal movable block;
a first guide portion formed on the first end plate toward the second end plate;
a second guide portion formed on the second end plate toward the first end plate to limit, by sliding between the first guide portion and the second guide portion, a movement direction in which the first end plate and the second end plate are moved close to or away from each other;
a bone screw configured to be inserted into bone screw holes formed in the first end plate and the second end plate; and
a locking member configured to be detachably fastened to the proximal movable block to prevent separation of the bone screw,
wherein the first guide portion and the second guide portion support a load in a length or width direction of the first end plate and the second end plate,
wherein the locking member comprises a locking plate configured to cover the bone screw and a locking bolt configured to be fixed to the proximal movable block through the locking plate,
wherein a locking-bolt coupling portion is formed on the proximal movable block such that the locking bolt is coupled to a front end of the adjustment, and
wherein the locking bolt is in contact with the adjustment member.

2. The intervertebral fusion cage of claim 1, wherein block sliders are formed on the distal movable block and the proximal movable block, and plate sliders slidable with respect to the block sliders are formed on the first and second distal plate slope portions and the first and second proximal plate slope portions.

3. The intervertebral fusion cage of claim 2, wherein the block sliders of the distal movable block are arranged on both sides of block slope portions corresponding to the first and second distal plate slope portions, auxiliary block sliders are arranged on outer sides of the block sliders, and auxiliary plate sliders corresponding to the auxiliary block sliders are formed on the first end plate and the second end plate.

4. The intervertebral fusion cage of claim 3, wherein reinforcing slope portions are formed on center portions of the block slope portions, and reinforcing slope portion seats corresponding to the reinforcing slope portions are formed on the first and second end plates.

5. The intervertebral fusion cage of claim 1, wherein the adjustment member comprises:
a threaded portion formed on an end thereof and configured to be screwed to the distal movable block; and
an adjustment member support surface formed on another end thereof and rotatable at a given position with respect to the proximal movable block.

6. The intervertebral fusion cage of claim 1, wherein the first guide portion comprises a pillar protruding toward the second end plate, and the second guide portion comprises an extension wall protruding toward the first end plate and slidable with respect to the pillar.

7. The intervertebral fusion cage of claim 6, wherein an accommodation portion is formed near the pillar to receive the extension wall when the first end plate and the second end plate are moved close to each other.

8. The intervertebral fusion cage of claim 7, wherein a guide recess is formed in the extension wall to guide insertion of the pillar.

9. The intervertebral fusion cage of claim 7, wherein a clearance cut portion is formed on the extension wall to prevent interference with the bone screw.

10. The intervertebral fusion cage of claim 1, wherein a locking protrusion protruding toward the bone screw is formed on a rear end of the locking plate.

11. The intervertebral fusion cage of claim 1, wherein the locking bolt in contact with the adjustment member pushes the adjustment member.

12. The intervertebral fusion cage of claim 1, wherein an anchor portion having no screw thread is formed on a distal end portion of the bone screw.

13. The intervertebral fusion cage of claim 12, wherein the anchor portion comprises an anchor groove extending in a length direction of the bone screw.

14. The intervertebral fusion cage of claim 13, wherein the anchor portion comprises an anchor protrusion protruding in radial directions.

* * * * *